United States Patent [19]
Chick et al.

[11] 4,439,442
[45] Mar. 27, 1984

[54] NAFTIDROFURYL CITRATE AND THERAPEUTIC APPLICATIONS

[75] Inventors: Jacques A. Chick, Sevres; Alain Heymes, Sisteron; Carlo Blasioli, Toulouse, all of France

[73] Assignee: SANOFI, Toulouse, France

[21] Appl. No.: 378,333

[22] Filed: May 14, 1982

[30] Foreign Application Priority Data

May 14, 1981 [FR] France ................. 81 09590

[51] Int. Cl.³ .................... A61K 31/34; C07D 307/16
[52] U.S. Cl. ..................................... 424/285; 549/496
[58] Field of Search ..................... 549/496; 424/285

[56] References Cited

U.S. PATENT DOCUMENTS 3,334,096  8/1967  Szarvasi et al. ............... 549/496 X Primary Examiner—Richard Raymond
Attorney, Agent, or Firm—Weiser, Stapler & Kimmelman

[57] ABSTRACT

The object of the invention is a new naftidrofuryl salt, naftidrofuryl citrate, which is therapeutically useful because it promotes metabolism and circulatory properties and because of its vaso-active properties in the treatment of arthritis of the limbs, Reynaud's Syndrome and cerebral circulatory insufficiency.

6 Claims, No Drawings

NAFTIDROFURYL CITRATE AND THERAPEUTIC APPLICATIONS

The present invention is related to a new naftidrofuryl salt, specifically naftidrofuryl citrate, which possesses toxicological, pharmacological, and clinical properties which are interesting and beneficial for therapeutic use.

The therapeutic use of naftidrofuryl oxalate in treating humans, is already known. It has properties as a metabolic and circulatory activator. This drug is also endowed with vasoactive properties by reason of its spasmolytic and sympatolytic effects.

Naftidrofuryl or diethylamino-2-ethyl 3-(1-naphthyl)-2- tetrahydrofurfurylpropionate, corresponds to the following formula:

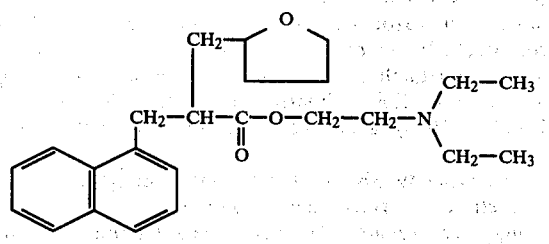

Thus, the object of the present invention is naftidrofuryl cirtrate, and the therapeutic application thereof.

A nonlimiting example of a procedure for preparing naftidrofuryl citrate will be described later in this diclosure. A comparative study of the two salts is also disclosed present. It especially concerns the determination of $LD_{50}$ in the mouse and the rat, the cardio-respiratory effects after perfusion in dogs and the bioavailability obtained in humans.

PROCEDURE FOR PREPARING NAFTIDROFURYL CITRATE

Naftidrofuryl citrate is prepared by a classical procedure of salification starting from the free base by utilizing citric acid monohydrate according to the mode of operation described hereafter.

There are mixed 2.5 liter of acetone, 2.5 liter of ethyl acetate, 500 g (1.30 mole) of naftidrofuryl purified base and 274 g (1.30 mole) of citric acid monohydrate, 2.5 of acetone and 2.5 liter of ethyl acetate. The mixture is brought to reflux liter and then cooled to about 5° C. The precipitate is filtered and dried.

Wt.: 640 g. (Yield: 85%)
M.P. about 84° C.

The compound is recrystallized in 4 liters of a mixture of acetone/ethyl acetate in proportions of 1:1 (v:v).

Wt.: 590 g. (Yield recrystallized: 92%) M.P.: about 86° C.

| Analysis ($C_{24}H_{33}NO_3C_6H_8O_7$) | | |
|---|---|---|
| | Calculated | Found |
| C | 62.59 | 62.01 |
| H | 7.18 | 7.13 |
| N | 2.43 | 2.48 |

The results of these toxicological, pharmacological, and clinical studies which are reported hereafter demonstrate the interesting properties of the compound of the invention.

I. TOXICOLOGICAL STUDY

These tests were performed on two types of animals, the mouse and the rat. Two modes of administration were used, a gastric tube and the intravenous route (i.v.).

I.1 Test on the Mouse

Each tested dose was administered to groups of 10 female mice of Swiss stock each weighing between 22 and 25 g. The two salts of naftidrofuryl were administered orally in a amount of 20 ml/kg. As a suspension of 5% of the salts in an aqueous solution of gum arabic. For intravenous route, a volume of 10 ml./kg of a solution of 0.9% of the salts in an aqueous solution of sodium chloride was administered. The $LD_{50}$ was calculated with the method of probits/ordinator.

I.1.1 Administration of gastric tube

The $LD_{50}/24$ h/kg. was 668.40 mg. for naftidrofuryl oxalate and 1,224.79 mg. for naftidroduryl citrate.

I.1.2 Intravenous administration

The $LD_{50}/24$ h/kg. was 18.40 mg. for naftidrofuryl oxalate and 22.28 mg. for naftidrofuryl citrate.

I.2 Tests on the Rat

The technique used was the same as that which was previously described for mice. Male rats of Wistar stock had a body weight of between 180 and 210 g. The volume administered orally was 15 ml./kg. and by injection 2 ml./kg.

I.2.1 Administration by gastric tube

The $LD_{50}/24$ h/kg. was 2,293.44 mg. of naftidrofuryl oxalate and 3,394.44 mg. for naftidrofuryl oxalate.

I.2.2 Intravenous administration;

The $LD_{50}/24$ h/kg. was 11.08 mg. for naftidrofuryl oxalate and 13.56 mg. for naftidrofuryl citrate.

A overall examination of all of these results readily shows a distinct difference, the better tolerance being in favor of naftidrofuryl citrate. Thus, for example, the $LD_{50}/24$ h/kh./p.o. of naftidrofuryl citrate is superior by 83.2 percent in mouse and by 48 percent in rat, in comparison with naftidrofuryl oxalate.

II. PHARMACOLOGICAL STUDY

The cardio-respiratory tests after perfusion were performed on 10 male Beagle dogs weighing between 13 and 16 kg.

The animals were placed under perfusion with administration of either naftidrofuryl oxalate or naftidrofuryl citrate at a concentration of 1.5 mg/kg.mn$^{-1}$ at [at rate of] 5 ml./mn, until the death of the animal. The tested products has been previously dissolved in an aqueous solution of sodium chloride at 9 parts/1000.

II.1 Experimental Protocol

After anesthesia with nembutal and chloralose, the arterial pressure was measured at the femoral and cartiod arteries by means of a Statham pressure gauge.

The electrocardiogram was recorded according to a standard derivation DII which permits the calculation of the duration of PR interval and cardiac frequency [heart rate] after treatment with a Narco biotachometer.

Venous pressure was controlled at the jugular vein by a Statham pressure gauge.

The variations of amplitude of the force of cardiac contractions [cardiac contractility] was measured by restraint gauge sewn on the left ventricle at the interventricular sulcus.

Three blood outflows, the femoral and the carotidal arterial flow and the cardiac flow at the ascending thoracic aorta, were measured by the same method which employed an electromagnetic metric flow meter. From this parameter, the cardiac work, of systolic ejection volume, and the total peripheral resistances have been calculated.

A thermocouple probe is placed at the exit of a tracheal cannula permitting the determination of the respiratory frequency and its amplitude.

All the parameters are recorded simultaneously on a Beckman polygraph.

II.2 Results

Under the experimental conditions described, the lethal dose of naftidrofuryl salts were determined.

II.2.1 Respiratory arrest was caused at 28±5 mg./kg. with naftidrofuryl oxalate and at 41±4 mg./kg with naftidrofuryl citrate.

II. 2.2 Cardiovascular collapse which followed occured with doses of 33±4 mg./kg. of naftidrofuryl oxalate and with 45±3 mg./kg. of naftidrofuryl citrate.

A distinct difference in favor of naftidrofuryl citrate with respect to causing respiratory arrest and cardiac failure is apparent. This study demonstrates the improved tolerance and contribution to improved cardiac and respiratory performances of naftidrofuryl citrate compared to naftidrofuryl oxalate. The cardiovascular parameters measured in the course of perfusion have shown like improvements.

To eliminate the possibility that the difference in effect of the tested compounds might be due to the oxalate or citrate portion [of the molecule], control tests were carried out in dogs which received either sodium oxalate or sodium citrate under the same experimental conditions as previously described. The perfusion was carried out for 50 minutes without the observed parameters displaying the least variation, although not a single dog which received either the oxalate or the citrate of naftidrofuryl, withstood [remained alive] perfusion for more than 25 minutes.

III. CLINICAL STUDY

III.1 Purpose of the Study

The purpose of this study is to compare the bioavailability in human patients of naftidrofuryl oxalate and naftidrofuryl citrate. The bioavailability is measured by concentration of the plasma and by the determination of the venous compliance [elasticity].

III.2 Method and Material

III.2.1 Subjects: the test was carried out on 12 subjects (9 males and 3 females) with a median age of 52.5 years.

III.2.2 Description of the study: Each subject received orally at least at an 8 day interval, either 300 mg. of either naftidrofuryl oxalate or naftidrofuryl citrate. The subjects were given no food for ten hours prior to taking the medication and 4 hours thereafter. Samples of venous blood were collected on heparin-fluoride; the concentration of naftidrofuryl in plasma was measured by the Fontaine et al. technique (Bull. Chim. Ther. 1969, 1, 44–49) at zero time (before administration), and at 0.5; 1; 1.5; 2; 3; 4; 6; 8 and 12 hours after the administration of one or the other naftidrofuryl salt. Furthermore, each half-hour following the administration of the tested products, the vasodilation resulting from one or the other naftidrofuryl salts was measured. This was done after vasoconstriction, by pre-administration of repeated administration of dihydroergotamine following the Thebault et al, technique (Comm. World Conference on Clinical Pharmacology and Therapeutics, London, 1980), a brief description of which is given here.

The procedure is based on the visual inspection of the diameter of a surface vein of the hand, under a standard congestive pressure. The predominant point of an appropriate vein on the back of the hand is marked with a cross with Indian ink. The subject, who is lying in a room at constant temperature has [body] member [part] its superior held in a rigid splint making a 30° angle with respect to the horizontal in a manner that the superficial "subcutaneous] veins are entirely collapsed. A binocular microscope whose optical axis is positioned exactly perpendicularly to the skin surface, is focused on the reference cross. One or two minutes after attaching a garrote, a determination is made and the superficial vein is considered totally vasodilated. Then the value of 100 is arbitrarily given to the diameter of the vein under examination. A dose of 2 mg. of dihydroergotamine (DHE) is then administered (zero time) and 90 minutes later (time 1.5), a dose of 0.5 mg. of DHE is administered each 30 minutes for the duration of the test (6 hours). These doses were from selected earlier tests which provided permanent vasoconstriction without the subject having secondary effects. At time 1.5, a single dose is administered to the subject in one single administration, of either 300 mg. of naftidrofuryl oxalate or 300 mg. of naftidrofuryl citrate. The diameter of the superficial vein is measured each half hour during the 6 hour period.

III.3 Results

The average of the results obtained are shown in the following Tables.

Table I deals with the concentration in blood and the areas under curves and Table II deals with the percentage of residual vasodilation.

TABLE I

| Product Administered | Blood Concentration Expressed in μg./ml T (h) | | | | | | | | | Area Under The Curves |
|---|---|---|---|---|---|---|---|---|---|---|
| | 0.5 | 1 | 1.5 | 2 | 3 | 4 | 6 | 8 | 12 | |
| Naftidrofuryl Oxalate | 1.22 | 1.11 | 0.69 | 0.58 | 0.24 | 0.13 | 0.05 | 0.02 | 0.01 | 2.56 |
| Naftidrofuryl | 2.90 | 2.47 | 1.68 | 1.05 | 0.60 | 0.42 | 0.24 | 0.08 | 0.02 | 6.30 |

TABLE I-continued

| | Blood Concentration Expressed in μg./ml | | | | | | | | |
|---|---|---|---|---|---|---|---|---|---|
| | T (h) | | | | | | | | |
| Product Administered | 0.5 | 1 | 1.5 | 2 | 3 | 4 | 6 | 8 | 12 | Area Under The Curves |
| Citrate | | | | | | | | | |

From examination of the results the following observations may be made.

III.3.1 Concentration in Blood

Examination of Table I shows that the bioavailability of naftidrofuryl citrate is not only distinctly greater than that of naftidrofuryl oxalate, but within the time shown is regardless at what time it is observed, the concentration of naftidrofuryl is always better for the citrate. The foregoing is confirmed by the areas under the curves which show an increase by 146 percent, always in favor of the citrate.

III.3.2 Vasodilation (Table II)

Again, a clear superiority of bioavailability has been established and one which is always in favor of naftidrofuryl citrate, and also, curiously enough, a clearly time-delayed effect. Whereas the maximum vasodilation is observed during the period of 0.5–1 hour for naftidrofuryl oxalate, it occurs during the period of 2.5–3 hours for naftidrofuryl citrate. Moreover, the areas under the vasodilation curves, expressed in the percentage of vaso-dilation multiplied by hours are respectively, an average of 145.5 for naftidrofuryl oxalate and on the average of 260.5 for naftidrofuryl citrate.

It follows from all of these experimental results described here that:

1. Toxicological conclusions

Naftidrofuryl citrate is clearly better tolerated than naftidrofuryl oxalate. The observed $LD_{50}$ was in favor of the naftidrofuryl citrate by significant proportions.

2. Pharmacological conclusions

The tolerance and the promotion of cardiac and respiratory activities of naftidrofuryl citrate are likewise greater than that of the oxalate.

3. Clinical conclusions

The bioavailability, which favors naftidrofuryl citrate over the oxalate, is confirmed by the areas under the curves. It is the same with respect to the vasodilation test of Thebault et al. Curiously enough, the maximum vasodilator has an effect with respect to naftidrofuryl citrate, but not with respect to naftidrofuryl oxalate, which has a retard effect.

The toxicological, pharmacological and clinical characteristics of naftidrofuryl citrate which are shown in relation to naftidrofuryl oxalate by a better tolerance, better activity, better bioavailability and a retard effect are in favor of the better suitability of naftidrofuryl citrate with regard to its therapeutic function, as for example in the treatment of arteritis of the limbs, Raynaud's Syndrome, and cerebral circulatory insufficiency.

The medication of the invention can be administered orally, in tablets, dragees, or gelatin capsules. Administration can also be parenterally by injectable solution for intramuscular or intravenous injection, or intravenous perfusion.

Each unitary dose advantageously contains between 0.010 g. to 0.500 g. of active material. The daily administrable doses can vary between 0.040 g. to 1.00 g of active material depending upon the age of the patient and the gravity of the treated afflication.

The following are given by way of non-limiting examples which illustrate pharmaceutical formulations of the medicaments of the invention.

(1) Tablet
Naftidrofuryl citrate: 0.200 g.
Excipient: corn starch, alginic acid, polyvidone, [polyvinylidone] magnesium stearate, talc.

(2) Sugar coated Tablets
Naftidrofuryl citrate: 0.150 g.
Excipient: talc, polyvinylpyrrolidone, magnesium stearate, gum arabic, glucose, white wax, carnauba wax, lactose, titanium oxide.

(3) Gelatin Capsules
Naftidrofuryl citrate: 0.050 g.
Excipient: talc, magnesium stearate (4) Injectable Solution
Naftidrofuryl citrate: 0.040 g.
Excipient istonic solvent q.s.p.: 5 ml.

We claim:

1. Naftidrofuryl citrate.

2. A pharmaceutical composition which has improved cardiovascular stimulanting properties including improved bioavailability and vasodilation, the vasodilation being of delayed and prolonged action which comprises an effective amount of the compound of claim 1 and a biologically acceptable carrier.

3. The pharmaceutical composition for oral administration in the form of tablets, sugar-coated tablets, gelatin capsules and for administration by the parenteral route as an injectable solution, the active ingredient being associated with an appropriate carrier.

4. The pharmaceutical composition is in the form of unitary doses containing from 0.010 to 0.500 g. of the active ingredient.

5. A method for promoting cardiovasular activity in a host which comprises administering to said host an effective amount of the compound of claim 1 and a biologically acceptable carrier and stimulating cardiovasular activity and vasodilation, the vasodilation being of delayed and prolonged effect.

6. The method of claim 5 wherein improved bioavailability is obtained upon administration and thereafter a prolonged vasodilation effect.

* * * * *

REEXAMINATION CERTIFICATE (710th)

United States Patent [19]

Chick et al.

[11] B1 4,439,442

[45] Certificate Issued    Jun. 30, 1987

[54] NAFTIDROFURYL CITRATE AND THERAPEUTIC APPLICATIONS

[75] Inventors: Jacques A. Chick, Sevres; Alain Heymes, Sisteron; Carlo Blasioli, Toulouse, all of France

[73] Assignee: SANOFI, Toulouse, France

Reexamination Request:
No. 90/001,023, Jun. 4, 1986

Reexamination Certificate for:
Patent No.: 4,439,442
Issued: Mar. 27, 1984
Appl. No.: 378,333
Filed: May 14, 1982

[30] Foreign Application Priority Data

May 14, 1981 [FR] France .................. 81 09590

[51] Int. Cl.⁴ ................ A61K 31/34; C07D 307/16
[52] U.S. Cl. ................................ 514/471; 549/496
[58] Field of Search ..................... 549/496; 514/471

[56] References Cited

U.S. PATENT DOCUMENTS

| 3,334,096 | 8/1967 | Szarvasi et al. ............. 549/496 X |
| 4,125,614 | 11/1978 | Lang et al. .................. 544/250 X |
| 4,380,639 | 4/1983 | Crenshaw et al. ............ 548/135 |

FOREIGN PATENT DOCUMENTS

| 0003199 | 9/1979 | European Pat. Off. . |
| 0003200 | 9/1979 | European Pat. Off. . |
| 0069664 | 8/1981 | European Pat. Off. . |
| 654M | 9/1960 | France . |
| 3843M | 3/1964 | France . |
| 1441524 | 3/1965 | France . |
| 2182886 | 3/1973 | France . |
| 2391997 | 5/1978 | France . |
| 2459241 | 6/1980 | France . |
| 2030985 | 4/1980 | United Kingdom . |

OTHER PUBLICATIONS

The Merck Index, 9th edition, 1976, pp. 253 and 843.

Primary Examiner—Richard Raymond

[57] ABSTRACT

The object of the invention is a new naftidrofuryl salt, naftidrofuryl citrate, which is therapeutically useful because it promotes metabolism and circulatory properties and because of its vaso-active properties in the treatment of arthritis of the limbs, Reynaud's Syndrome and cerebral circuitry insufficiency.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-6 are cancelled.

* * * * *